United States Patent
Sawaki et al.

(10) Patent No.: US 7,105,684 B2
(45) Date of Patent: Sep. 12, 2006

(54) LACTONE COMPOUNDS

(75) Inventors: Tomoya Sawaki, Hiratsuka (JP); Hiroyuki Kenmochi, Hiratsuka (JP); Yoji Hori, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 248 days.

(21) Appl. No.: 10/899,965

(22) Filed: Jul. 26, 2004

(65) Prior Publication Data

US 2005/0059830 A1 Mar. 17, 2005

(30) Foreign Application Priority Data

Jul. 25, 2003 (JP) .............................. 2003-279613

(51) Int. Cl.
- *C07D 313/00* (2006.01)
- *C07D 493/08* (2006.01)
- *C07D 307/77* (2006.01)
- *C07C 69/74* (2006.01)

(52) U.S. Cl. ...................... 549/266; 549/268; 549/271; 549/300; 560/117

(58) Field of Classification Search ................ 549/266, 549/268, 271, 300; 560/117
See application file for complete search history.

(56) References Cited

U.S. PATENT DOCUMENTS

| 6,280,898 B1 | 8/2001 | Hasegawa et al. |
| 2001/0026901 A1 | 10/2001 | Maeda et al. |

FOREIGN PATENT DOCUMENTS

| JP | 2000-26446 | 1/2000 |
| JP | 2000/26446 | * 1/2000 |
| JP | 2000-159758 | 6/2000 |

* cited by examiner

*Primary Examiner*—Kamal A. Saeed
*Assistant Examiner*—Joseph R. Kosack
(74) *Attorney, Agent, or Firm*—Peter F. Corless; Christine C. O'Day; Edwards Angell Palmer & Dodge LLP

(57) ABSTRACT

An object of the present invention is to provide a novel monomer compound having a lactone structure which gives polymers having more excellent feature as resist material, etc.

The present invention relates to a compound represented by the following formula [1]:

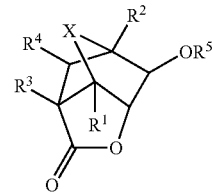

[1]

wherein $R^1$ and $R^2$ are an alkyl group; $R^3$ and $R^4$ are each independently hydrogen atom or an alkyl group; $R^5$ is hydrogen atom, acryloyl group or methacryloyl group; and X is a methylene group which may have an alkyl group or an ethylene group which may have an alkyl group.

The present invention provides a compound having a lactone structure which gives a polymer having more excellent feature particularly as a resist material and also provides a hydroxy lactone being useful as a material, etc. therefor.

3 Claims, 3 Drawing Sheets

LACTONE COMPOUNDS

1. TECHNICAL FIELD

The present invention relates to a compound having a lactone structure which is useful as a constituting monomer, etc. for the resin used for coating, adhesive, binder, resin for ink, resist, etc. and also to a hydroxy lactone which is useful as a material, etc. therefor.

2. BACKGROUND OF THE INVENTION

In the field of semiconductors, tendency for a high integration is more and more progressing in recent years and various properties are also required for resist materials used therefor. Examples of the required properties are hydrophobicity, heat resistance, appropriate polarity and appropriate solubility in various organic solvents as well as transparency and stability. With regard to substances having such properties, development for compounds having a lactone structure has been well-carried out in recent years. For example, (meth) acrylate compounds having a tricyclic lactone structure are disclosed in JP-A-2000-26446 and JP-A-2000-159758.

3. SUMMARY OF THE INVENTION

Although all of the (meth)acrylate compounds having a tricyclic lactone structure mentioned in JP-A-2000-26446 and JP-A-2000-159758, etc. give polymers showing excellent etching resistance and adhesion to substrate, there has still been need for monomers giving polymers that have more excellent properties. Accordingly, an object of the present invention is to provide a novel monomer compound having a lactone structure which gives polymers having more excellent properties as resist materials, etc.

In view of the above object, the inventors have carried out extensive studies and, as a result, they have found that specific polycyclic compounds are able to solve the above problem whereupon the present invention has been accomplished.

Thus, the present invention relates to a compound represented by the following formula [1]:

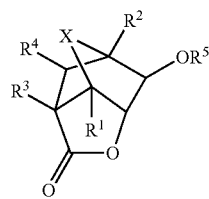

[1]

wherein $R^1$ and $R^2$ are an alkyl group; $R^3$ and $R^4$ are each independently hydrogen atom or an alkyl group; $R^5$ is hydrogen atom, acryloyl group or methacryloyl group; and X is a methylene group which may have an alkyl group or an ethylene group which may have an alkyl group.

The present invention provides a novel monomer compound having a lactone structure which gives a polymer having more excellent characteristics as, for example, a resist material and also provides an alcohol having a lactone structure being useful as a material, etc. therefor. The monomer according to the present invention has, for example, the following excellent features.

i) It has a heat resistance and an appropriate polarity, has an appropriate hydrophobicity due to introduction of alkyl group into 1- and 7-positions of a tricyclic ring and has a solubility in organic solvents suitable for the manufacture of (co)polymers by means of a solution polymerization.

ii) (Co)polymer which is prepared by (co)polymerization of the monomer of the present invention also has an excellent solubility in solvents due to introduction of alkyl group into 1- and 7-positions of a tricyclic ring and, since it is freely soluble in propylene glycol monomethyl ether acetate (2-acetoxy-1-methoxypropane), methyl ethyl ketone, methyl isobutyl ketone, etc. which have been commonly used as solvents suitable for resist, a uniform coating is possible when a resist material using the polymer as a base resin is coated (spin coated) on a silicone substrate.

iii) A resist material using the monomer of the present invention as a base resin is useful in a fine processing by far-ultraviolet ray and electronic ray such as ArF excimer laser and KrF excimer laser whereupon more precise pattern is able to be formed upon the manufacture of semiconductors.

4. BRIEF DESCRIPTION OF THE DRAWINGS

5. DETAILED DESCRIPTION OF THE INVENTION

Figure 1:
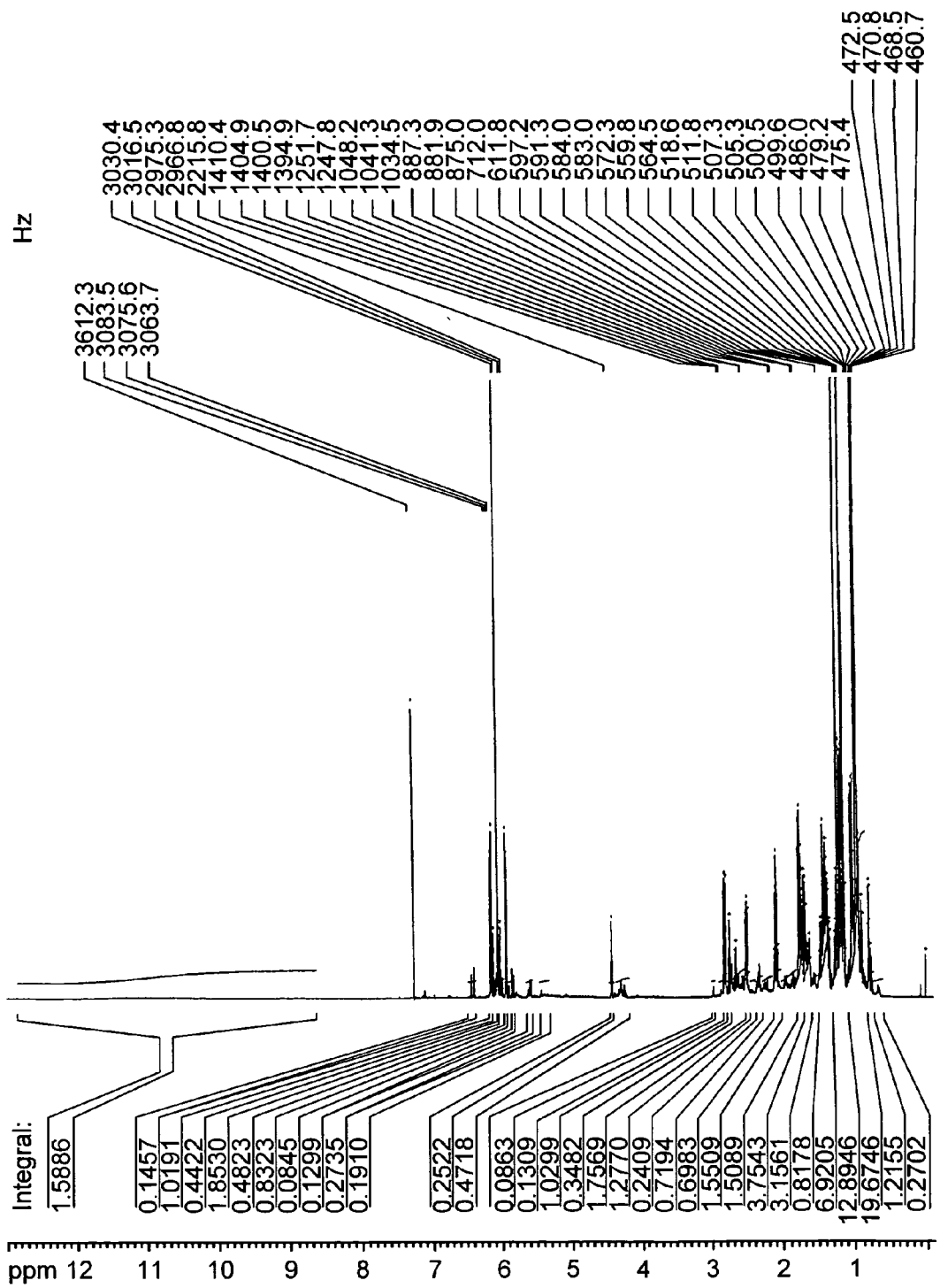
FIG. 1 shows a $^1$H-NMR spectrum in chloroform-d of the crude product prepared in (1) of Example 1 (numerals written below the spectrum indicate the integral value).

In the compound of the present invention represented by the above formula [1], the alkyl group represented by $R^1$ and $R^2$ and the alkyl group when $R^3$ and $R^4$ are alkyl groups are straight or branched alkyl groups having 1 to 8 or, preferably, 1 to 4 carbon atoms. Specific examples of the alkyl groups include methyl group, ethyl group, n-propyl group, isopropyl group, n-butyl group, sec-butyl group, isobutyl group and tert-butyl group.

Among those alkyl groups, particularly preferred alkyl groups are methyl group, ethyl group and isopropyl group.

The alkyl group in the methylene group which may have an alkyl group or the ethylene group which may have an alkyl group in the compound of the present invention represented by the formula [1] may be same as in the above $R^1$, $R^2$, $R^3$ and $R^4$ and the particularly preferred alkyl group may be the same as described above.

The compound represented by the general formula [1], wherein $R^5$ is acryloyl group or methacryloyl group can be used for constituting monomer for resin which is used as coating, adhesive, binder, resin for ink, resist, etc. while the compound represented by the general formula [1], wherein $R^5$ is hydrogen atom is an alcohol having a lactone structure useful as a starting material.

In the compound of the present invention represented by the formula [1] include isomers such as endo- and exo-substance isomers.

The compound of the present invention represented by the formula [1] may be easily produced according to the following reaction scheme:

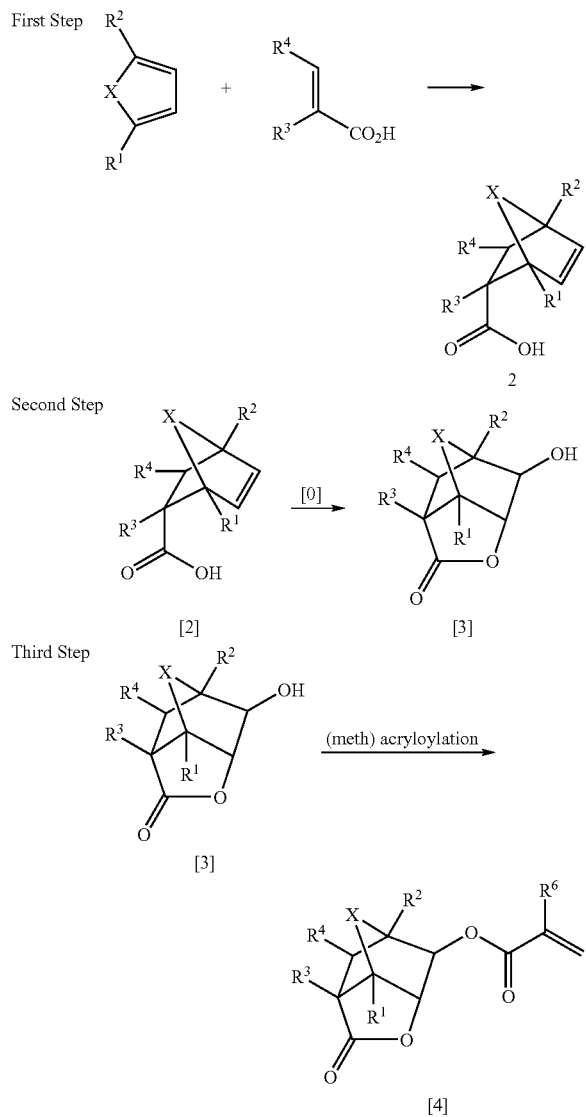

wherein $R^1$, $R^2$, $R^3$ and $R^4$ represent the same meanings as defined above and $R^6$ is hydrogen atom or methyl group.

Thus, a cyclic olefin [2] having a carboxyl group which is a Diels-Alder adduct is prepared from a cyclic diene compound and an α,β-unsaturated carboxylic acid in the first step, and then, a lactonization is carried out under an oxidative condition to give the compound of the present invention where $R^5$ is hydrogen atom in the formula [1] or an alcohol [3] having a lactone structure in the second step.

Then the alcohol (hydroxylactone) [3] is subjected to a (meth)acryloylation (esterification) using a (meth)acryloylating agent to give the compound of the present invention where $R^5$ is acryloyl group or methacryloyl group in the formula [1] or a (meth)acrylate [4] in the third step.

Each of the steps will be now illustrated in detail.

First Step: Diels-Alder Reaction of a Conjugated Cyclic Diene Compound with an α,β-unsaturated Carboxylic Acid A cyclic olefin having a carboxyl group represented by the formula [2] is able to be prepared by a Diels-Alder reaction of a conjugated cyclic diene compound with an α,β-unsaturated carboxylic acid. This reaction is usually carried out by heating in a pressure-resistant closed vessel such as an autoclave using a solvent which is inert to the reaction. The reaction temperature is about 60 to 200° C. and, if necessary, an open system may be adopted using a refluxing condenser or the like. Examples of the conjugated cyclic diene compound used herein are cyclopentadiene, an alkyl-substituted cyclopentadiene, 1,3-cyclohexadiene, an alkyl-substituted cyclohexadiene and a $C_{10-20}$ conjugated diene compound having a six-membered ring structure.

Examples of the alkyl-substituted cyclopentadiene are 1-methylcyclopentadiene, 5,5-dimethylcyclopentadiene and 1,4-dimethylcyclopentadiene. More specific examples of the conjugated diene compound having a six-membered ring structure are α-terpinene, etc.

The resulting Diels-Alder adduct [2] is able to be isolated and purified by common methods such as distillation, crystallization and various kinds of chromatography.

Second Step: Lactonization

The lactone represented by the formula [3] having a hydroxyl group (hydroxy lactone) is able to be prepared by a lactonization of a cyclic olefin represented by the formula [2] having a carboxyl group under an oxidative condition.

The reaction may be carried out according to well known methods such as a method mentioned in *J. Chem. Soc., Perkin Trans.* 1, page 1065 (1998). Thus, it is recommended that the cyclicolefincarboxylic acid [2] is treated by using, preferably, formic acid or the like as a solvent as well as a reactant and by adding hydrogen peroxide as an oxidizing agent under, if necessary, heating or cooling.

With regard to the reaction temperature, the range of 0 to 50° C. is preferred and the range of 10 to 40° C. is more preferred. When the reaction temperature is higher than 50° C., there may be the case where the yield lowers due to autolysis of hydrogen peroxide while, when the reaction temperature is lower than 0° C., the reaction rate becomes slow, which is not preferred.

Although the reaction may be carried out under an air atmosphere, it is preferred to be carried out under an atmosphere of inert gas such as nitrogen or argon.

Although the hydroxy lactone prepared as such may be purified by crystallization, various chromatography, etc., it is also possible that the lactone is subjected to the next step without purification.

Third Step: Esterification

Esterification is carried out by the reaction of the hydroxylactone [3] prepared as above with a (meth)acryloylating agent such as (meth)acryloyl chloride and (meth)acrylic anhydride. The reaction is generally carried out in the presence of a base, which is preferably an organic base, particularly preferably a tertiary amine. Specific examples of the base are an aliphatic amine such as triethylamine, diisopropylethylamine, N-methylmorpholine and N-methylpiperidine and an aromatic amine such as pyridine and α-, β- or γ-picoline.

Amount of the base used with respect to the alcoholic substance [3] is 1.0 to 2.0 parts by mol or, preferably, 1.0 to 1.5 parts by mol.

Amount of the (meth)acryloylating agent used with respect to the hydroxy lactone [3] which is a substrate is 1.0 to 2.0 parts by mol or, preferably, 1.0 to 1.5 parts by mol.

In the esterification reaction, it is preferred to use a solvent and, with regard to the solvent used, any solvent may be used so far as it has no adverse affects on the esterification. Specifically, an aromatic hydrocarbon such as toluene and xylene and a cyclic or a non-cyclic ether such as tetrahydrofuran (THF) and dimethoxyethane may be used as preferred solvents.

The reaction temperature may be from −20° C. to 100° C. and, preferably, from 0° C. to 60° C.

In order to prevent the polymerization upon after-treatment or purification, it is preferred to use a polymerization inhibitor and, for example, a phenolic compound such as hydroquinone and 4-methoxyphenol or an N-oxyl type compound such as 4-hydroxy-2,2,6,6-tetramethylpiperidine-N-oxyl may be used.

Specific examples of the compound of the present invention where $R^5$ in the formula [1] is acryloyl group or methacryloyl group obtained in the above manner are illustrated below.

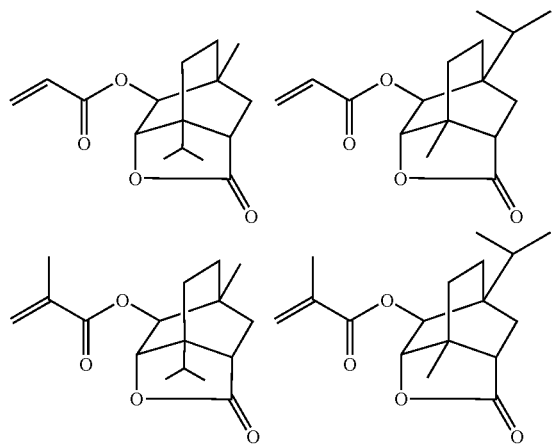

Further, specific examples of the compounds of the present invention (hydroxy lactone) wherein $R^5$ in the formula [1] is hydrogen atom are illustrated below.

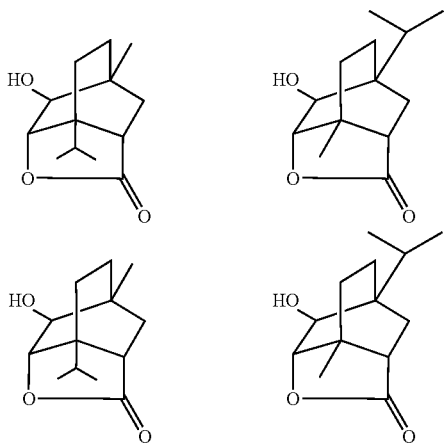

In production of the compound of the present invention, various steric isomers including exo- and endo-substances are usually generated during the stage of Diels-Alder reaction and, therefore, the product is prepared as a mixture of isomers in any of the cases of the above hydroxy lactone and the compound prepared by (meth)acryloylation thereof. Although it is possible to separate into each isomer by means of an operation such as column chromatography if necessary, the compound in a form of a mixture is usually able to be used as a monomer giving a polymer which is advantageous as a base resin for resist materials.

The compound of the present invention wherein $R^5$ is acryloyl group or methacryloyl group in the formula [1] is a (meth) acrylate compound having a cross-linked ring structure and a γ-butyrolactone structure in the same molecule and has alkyl groups such as methyl and isopropyl groups at both ends of the cross-linked bridge. Because of the structure as such, the compound of the present invention has a heat resistance and an appropriate polarity, as well as an appropriate hydrophobicity due to introduction of plural alkyl groups, and it further has a solubility in organic solvents which are suitable for the manufacture of (co) polymers by a solution polymerization. The polymer prepared by the polymerization also has an excellent solubility in a solvent due to the plural alkyl groups which are introduced in the same manner. For example, it is very easily dissolved in propylene glycol monomethyl ether acetate (2-acetoxy-1-methoxypropane), methyl ethyl ketone, methyl isobutyl ketone, etc. which are commonly used as appropriate solvents for resist. Therefore, when a resist material where the polymer is used as a base resin is applied on a silicone substrate (such as by a spin coating method), a uniform coating is possible.

A resist material in which the polymer is used as a base resin is useful for a fine processing by far-ultraviolet ray or electronic ray such as ArF excimer laser and KrF excimer laser and, in the manufacture of semiconductors, more highly precise pattern is able to be formed.

The compound of the present invention wherein $R^5$ is hydrogen atom in the formula [1] (hydroxy lactone) is useful as a material, etc. for the compound of the present invention where $R^5$ is (meth)acryloyl group in the formula [1].

The present invention will now be more specifically illustrated by way of the following Examples although the present invention is never limited by those Examples.

Incidentally, $^1$H-NMR spectra were measured by the following instrument.

$^1$H-NMR spectrum: Apparatus of type DRX-500 (manufactured by Bruker)

Internal Standard:tetramethylsilane

EXAMPLE 1

Synthesis of a mixture of 2-methacryloyloxy-1-isopropyl-7-methyl-4-oxatricyclo[4,3,1,0$^{3,7}$]decan-5-one and 2-methacryloyloxy-7-isopropyl-1-methyl-4-oxatricyclo[4,3,1, 0$^{3,7}$]-decan-5-one (1) Synthesis of a mixture of 4-isopropyl-1-methyl-bicyclo[2,2,2]-5-decene-3-carboxylic acid, 1-isopropyl-7-methylbicyclo[2,2,2]-5-decene-3-carboxylic acid, 4-isopropyl-1-methylbicyclo[2,2,2]-5-decene-2-carboxylic acid and 1-isopropyl-7-methylbicyclo[2,2,2]-5-decene-2-carboxylic acid

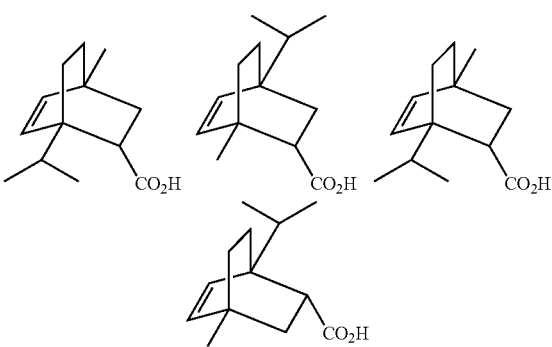

Acrylic acid (400 g, 5.5509 mol) was charged in a 2000-mL reaction flask equipped with a refluxing condenser, then α-terpinene (924.31 g; purity: 90%; amount of pure α-terpinene: 831.88 g; 1.1 equivalents to acrylic acid) was poured thereinto at room temperature and the mixture was made to react at 160° C. for 6 hours. After completion of the reaction, low-boiling substances were evaporated under reduced pressure to give 1079.5 g of the aimed product of 96.7% purity. Yield in terms of the pure substance was 90.2%. The crude product per se was subjected to the reaction of the next step.

$^1$H-NMR spectrum of the crude product in chloroform-d is shown in FIG. 1.

(2) Synthesis of a mixture of 2-hydroxy-1-isopropyl-7-methyl-4-oxatricyclo[4,3,1,0$^{3,7}$]decan-5-one and 2-hydroxy-7-isopropyl-1-methyl-4-oxatricyclo[4,3,1,0$^{3,7}$]-decan-5-one

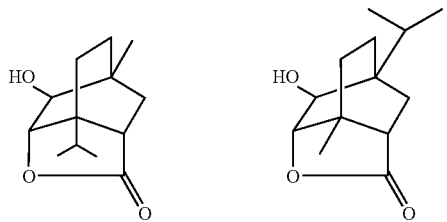

The Diels-Alder adduct (DA adduct) (900 g, 4.321 mol) prepared in the above (1) was dissolved in 437.5 g of formic acid (9.506 mol; 2.2 equivalents to the DA adduct), 538.8 g (4.735 mol; 110 molar % to the DA adduct) of a 30% aqueous solution of hydrogen peroxide was dropped thereinto at 50° C. or less and the reaction was carried out at 40° C. for 20 hours. After completion of the reaction, the reaction solution was poured into a 35% aqueous solution of sodium sulfite (4154.4 g; 11.536 mol; 267 molar % to the DA adduct). An aqueous layer was extracted with 2,700 mL of ethyl acetate three times and the organic layer was washed with water and concentrated under reduced pressure. The resulting residue was dissolved in 2,700 mL of methanol, a catalytic amount of potassium carbonate was added thereto and the mixture was stirred at room temperature for 3 hours. After evaporation of methanol under reduced pressure, the aimed product was dissolved in 5,400 mL of toluene to give 4,625 g of solution of a hydroxy-lactone substance in toluene (concentrated substance: 793.61 g; purity: 77.01%; amount of the pure substance: 611.2 g; yield: 63.1%).

Figure 2:
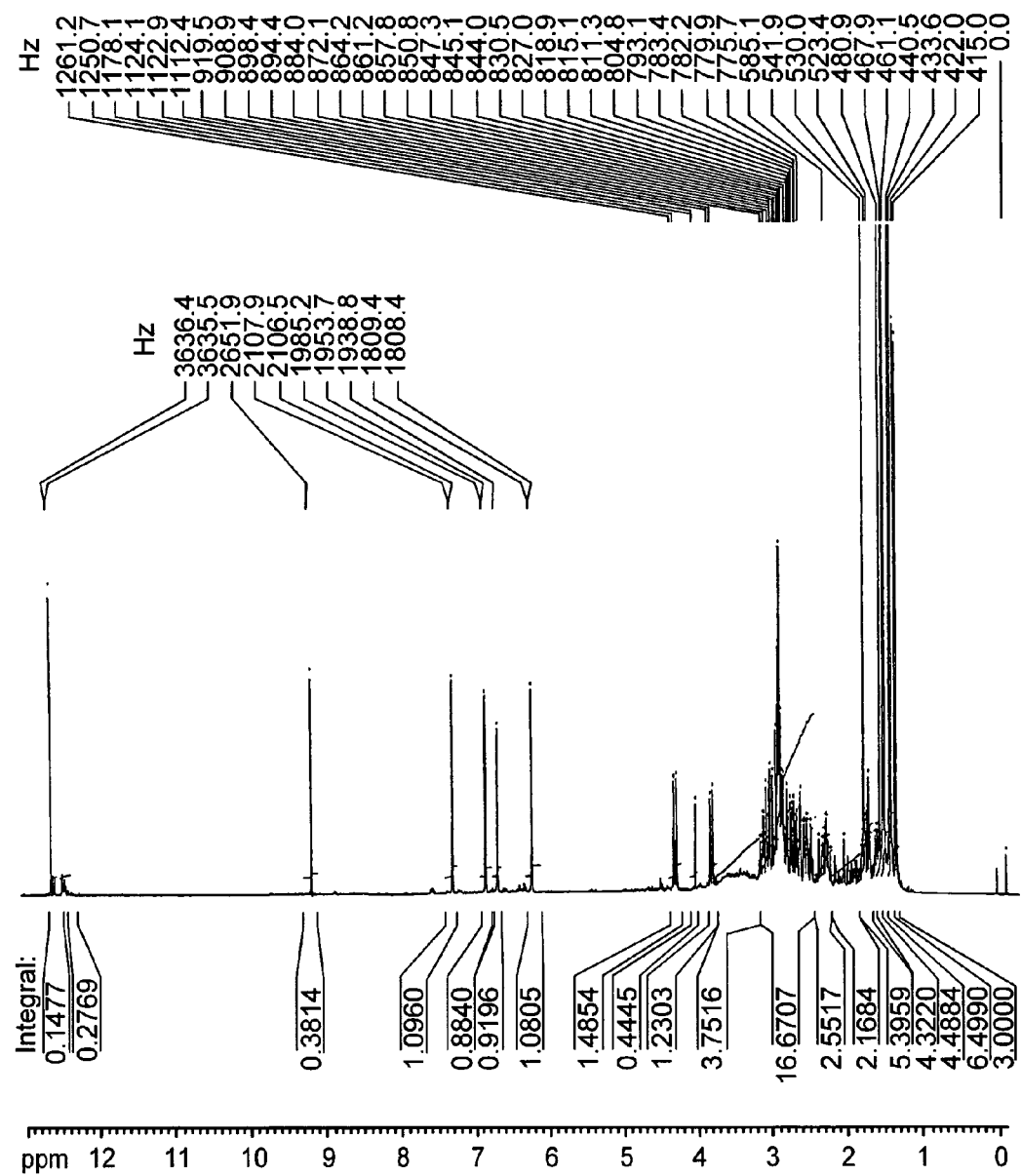
FIG. 2 shows a $^1$H-NMR spectrum in chloroform-d of the crude product prepared in (2) of Example 1 (numerals written below the spectrum indicate the integral value).

$^1$H-NMR spectrum of the resulting crude product in chloroform-d is shown in FIG. 2.

(3) Synthesis of a mixture of 2-methacryloyloxy-1-isopropyl-7-methyl-4-oxatricyclo[4,3,1,0$^{3,7}$] decan-5-one and 2-methacryloyloxy-7-isopropyl-1-methyl-4-oxatricyclo-[4,3,1,0$^{3,7}$] decan-5-one

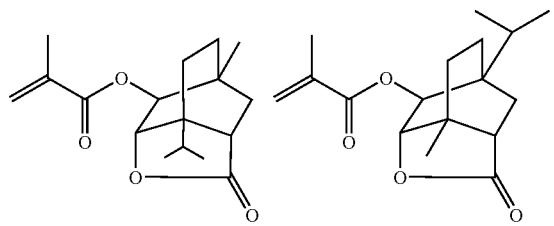

Under nitrogen atmosphere, 281.7 g (50 gas a pure hydroxy substance; 0.2292 mol) of solution of the hydroxy-lactone substance in toluene prepared in the above (2) and 1.4 g of 4-dimethylaminopyridine was added to a 1000-mL reaction flask, the mixture was cooled at 10° C. or less, 96 g of a solution of methacrylic anhydride in toluene (amount of methacrylic anhydride: 53.0 g; 0.3437 mol) was added thereto and 39.4 g of triethylamine was dropped thereinto. After the dropping, the mixture was stirred at room temperature for 20 hours and the reaction was stopped by addition of 5.1 g of in ethanol. After that, 198.7 g of a 10% aqueous solution of sulfuric acid was added there to and the mixture was stirred for 10 minutes and separated. The organic layer was washed with water once and washed with 475.1 g of a 10% aqueous solution of potassium carbonate and then the washing with water was carried out three times. An N-oxyl compound and hydroquinone monomethyl ether were added as polymerization inhibitors, toluene was recovered by concentration under reduced pressure and the residue was distilled under reduced pressure (153 to 155° C./16.0 Pa) to give 33.0 g of the aimed product. Yield was 51.6%.

Figure 3:
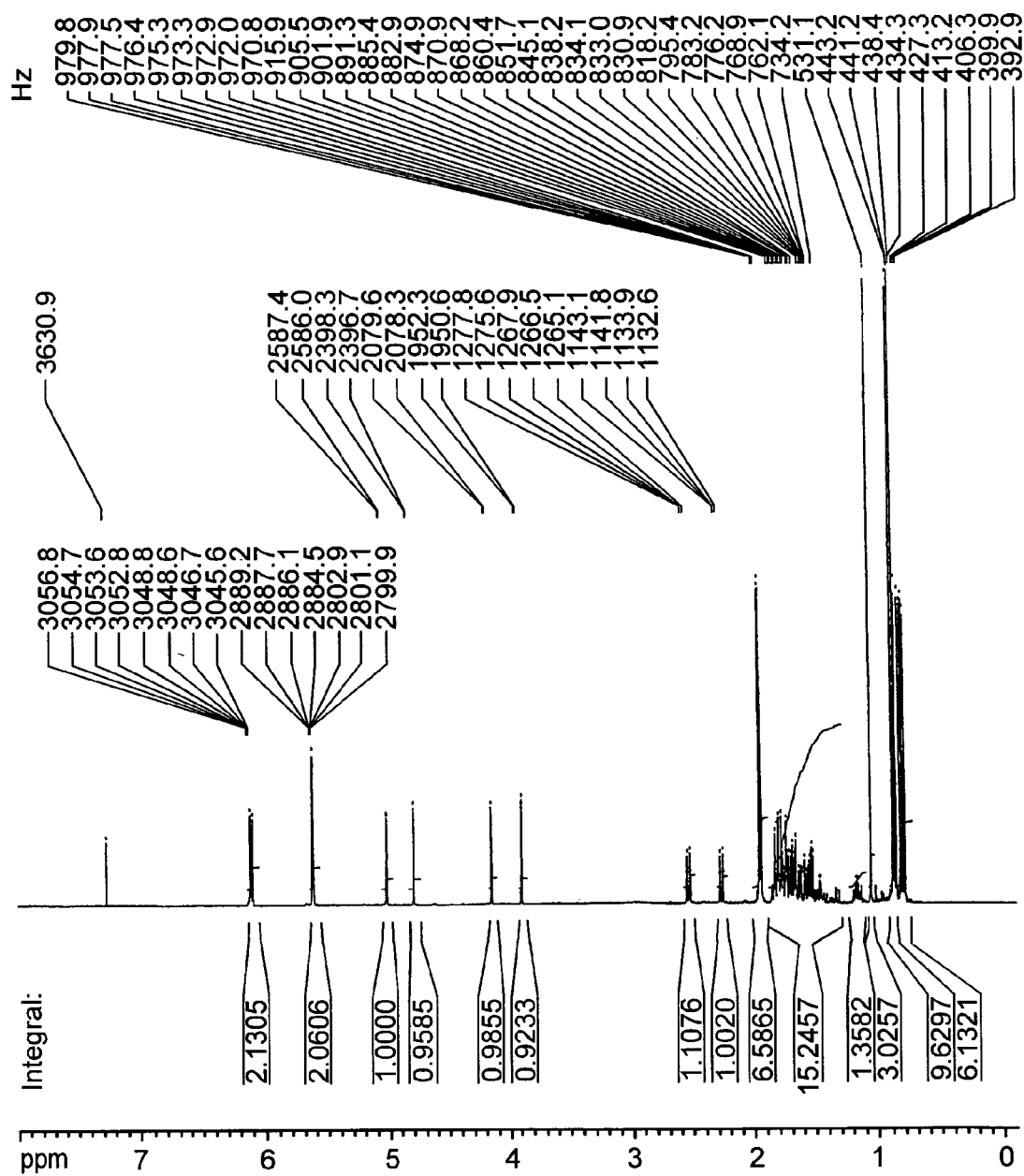
FIG. 3 shows a $^1$H-NMR spectrum in chloroform-d of the aimed product prepared in (3) of Example 1 product purified by distillation (numerals written below the spectrum indicate the integral value).

$^1$H-NMR spectrum of the distilled pure product in chloroform-d is shown in FIG. 3.

The novel monomer having a lactone structure according to the present invention is able to be utilized as a constituting monomer, etc. for resin used, for example, as coating, adhesive, binder, resin for ink, resist material, etc. and is particularly useful as a constituting monomer for resin for resist material used for a fine processing by far-ultraviolet ray, electronic ray, etc. such as ArF excimer laser and KrF excimer laser and. When a resist material using the monomer according to the present invention is used as a base resin, more highly precise pattern formation can be expected in the manufacture of semiconductors. Further, the hydroxy lactone according to the present invention is useful as a material, etc. for the above monomer.

What is claimed is:

1. A compound represented by the following formula [1]:

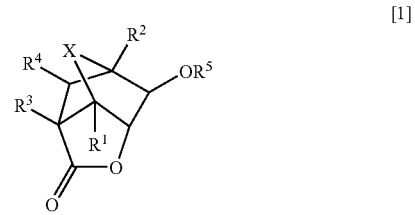

wherein $R^1$ and $R^2$ are an alkyl group with the proviso that $R^1$ and $R^2$ can each independently be a methyl group, but may not simultaneously be methyl groups; $R^3$ and $R^4$ are each independently hydrogen atom or an alkyl group; $R^5$ is hydrogen atom, acryloyl group or methacryloyl group; and X is a methylene group which may have an alkyl group or an ethylene group which may have an alkyl group.

2. The compound according to claim 1, wherein $R^5$ in the formula [1] is an acryloyl group or a methacryloyl group.

3. The compound according to claim 1, wherein $R^5$ in the formula [1] is hydrogen atom.

* * * * *